United States Patent [19]

Goto et al.

[11] Patent Number: 5,466,660
[45] Date of Patent: Nov. 14, 1995

[54] TETRAZOLINONES AS HERBICIDES FOR USE IN PADDY

[75] Inventors: Toshio Goto; Hidenori Hayakawa, both of Tochigi; Yukiyoshi Watanabe, Saitama; Shin-ichi Narabu, Ibaragi; Akihiko Yanagi, Tochigi, all of Japan

[73] Assignee: Nihon Bayer Agrochem K.K., Tokyo, Japan

[21] Appl. No.: 230,949

[22] Filed: Apr. 21, 1994

Related U.S. Application Data

[62] Division of Ser. No. 86,606, Jul. 1, 1993, Pat. No. 5,347,010.

[30] Foreign Application Priority Data

Jul. 9, 1992 [JP] Japan .................. 4-204271
Oct. 29, 1992 [JP] Japan .................. 4-312607

[51] Int. Cl.⁶ .................. A01N 43/713
[52] U.S. Cl. .................. 504/134; 504/136; 504/139; 504/261
[58] Field of Search .................. 504/261, 139, 504/134, 136

[56] References Cited

U.S. PATENT DOCUMENTS

| | | | |
|---|---|---|---|
| 4,618,365 | 10/1986 | Covey et al. | 71/92 |
| 4,826,529 | 5/1989 | Covey et al. | 71/92 |
| 4,830,661 | 5/1989 | Covey et al. | 71/92 |
| 4,956,469 | 9/1990 | Covey et al. | 548/251 |
| 5,003,075 | 3/1991 | Covey et al. | 548/251 |
| 5,019,152 | 5/1991 | Covey et al. | 71/92 |

FOREIGN PATENT DOCUMENTS

0146279  6/1985  European Pat. Off. .

OTHER PUBLICATIONS

*Farm Chemicals Handbook* "Besylfuran–methyl" C34 1987.
Pestic. Sci., 1990, vol. 30, pp. 259–274.
1987 British Crop Protection Conference–Weeds, pp. 249–255.

Primary Examiner—S. Mark Clardy
Attorney, Agent, or Firm—Sprung Horn Kramer & Woods

[57] ABSTRACT

Compositions comprising herbicidal tetrazolinones of the formula (I)

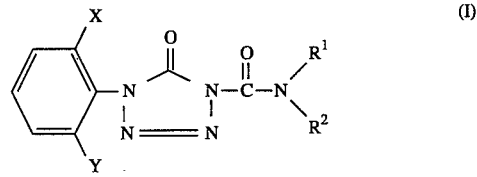

wherein X is chlorine or bromine,
Y is hydrogen, chlorine, bromine, methyl or ethyl, and
$R^1$ and $R^2$ are the same or different $C_{2-4}$ alkyl,
and at least one additional herbicide.

17 Claims, No Drawings

TETRAZOLINONES AS HERBICIDES FOR USE IN PADDY

This application is a divisional, of application Ser. No. 08/086,606, filed Jul. 1, 1993 now U.S. Pat. No. 5,347,010.

The present invention relates to novel tetrazolinones, to a process for the preparation thereof, and to their use as paddy-herbicides.

It has already been disclosed that tetrazolinone derivatives have herbicidal properties (see U.S. Patents Nos. 4,956,469, 5,003,075 and 5,019,152 or the corresponding European Applications EP-A-146,279 and EP-A-202,929).

There have now been found novel tetrazolinones of the formula (I)

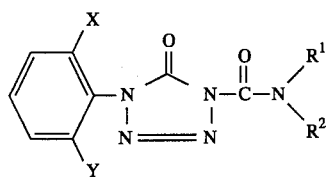

(I)

wherein X is chlorine or bromine,

Y is hydrogen, chlorine, bromine, methyl or ethyl, and $R^1$ and $R^2$ are the same or different $C_{2-4}$ alkyl.

The compounds of the formula (I) can be obtained by a process in which a) compounds of the formula (II)

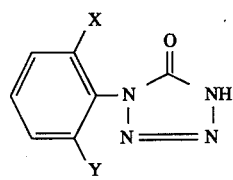

(II)

wherein X and Y have the same meanings as mentioned before, are reacted with compounds of the formula (III)

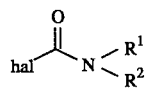

(III)

wherein $R^1$ and $R^2$ have the same meanings as mentioned above, and hal is an eliminating group such as chlorine, bromine and the like, in the presence of inert solvents, and if appropriate, in the presence of an acid binder.

The novel tetrazolinones (I) exhibit powerful herbicidal properties, in particular against paddy-field weeds. While the compounds of the formula (I), according to the invention, generically fall within the scope of the aforementioned U.S. and EP patent rights, the compounds of the formula (I) have not been specifically disclosed in these references.

And, surprisingly, the compounds of the formula (I) exhibit a substantially much greater herbicidal action against paddy-weeds than those specifically known from the references.

Among the compounds of the formula (I), according to the invention, preferred compounds are those in which X is chlorine, Y is hydrogen, chlorine or methyl, and $R^1$ and $R^2$ are the same or different ethyl, n-propyl, isopropyl, n-butyl, isobutyl or sec-butyl.

Specifically, the following compounds, in addition to the compounds mentioned in the examples, may be mentioned hereinafter:

1-(2-chlorophenyl)-4-(N,N-diethylcarbamoyl)-5(4H)-tetrazolinone, 1-(2,6-dichlorophenyl)-4-(N,N-di-n-propylcarbamoyl)-5(4H-)tetrazolinone, 1-(2-chloro-6-methylphenyl)-4-(N,N-di-n-propylcarbamoyl)-5(4H)-tetrazolinone, 1-(2-bromophenyl)-4-(N,N-diethylcarbamoyl)-5(4H)-tetrazolinone, 1-(2-chloro-6-ethylphenyl)-4-(N,N-diethylcarbamoyl)-5(4H)-tetrazolinone, 1-(2-chlorophenyl)-4-(N-ethyl-N-n-propylcarbamoyl)-5(4H)-tetrazolinone, 1-(2-chlorophenyl)-4-(N,N-di-n-propylcarbamoyl)-5(4H)-tetrazolinone, 1-(2,6-dichlorophenyl)-4-(N,N-diethylcarbamoyl)-5(4H)-tetrazolinone, 1-(2,6-dichlorophenyl)-4-(N-ethyl-N-n-propylcarbamoyl)-5(4H)-tetrazolinone, 1-(2-chloro-6-methylphenyl)-4-(N,N-diethylcarbamoyl)-5(4H)-tetrazolinone, 1-(2-chloro-6-methylphenyl)-4-(N-ethyl-N-n-propylcarbamoyl) -5(4H)-tetrazolinone, 1-(2-bromophenyl)-4-(N-ethyl-N-n-propylcarbamoyl)-5(4H)-tetrazolinone, 1-(2-bromophenyl)-4-(N,N-di-n-propylcarbamoyl)-5(4H)-tetrazolinone, 1-(2,6-dibromophenyl)-4-(N,N-diethylcarbamoyl)-5(4H)-tetrazolinone, 1-(2,6-dibromophenyl)-4-(N-ethyl-N-n-propylcarbamoyl)-5(4H)-tetrazolinone, 1-(2,6-dibromophenyl)-4-(N,N-di-n-propylcarbamoyl)-5(4H)-tetrazolinone, 1-(2-chloro-6-methylphenyl)-4-(N-n-butyl-N-ethylcarbamoyl)-5(4H)-tetrazolinone, 1-(2-chloro-6-methylphenyl)-4-(N-n-propyl-N-ethylcarbamoyl)-5(4H)-tetrazolinone, and 1-(2-chloro-6-methylphenyl)-4-(N-sec-butyl-N-n-propylcarbamoyl)-5(4H)-tetrazolinone.

If use is made, in the above-mentioned process a), of 1-(2-chlorophenyl)-5(4H)-tetrazoline and diethylcarbamoyl chloride, as the starting materials, for example, the reaction can be expressed by the following reaction equation:

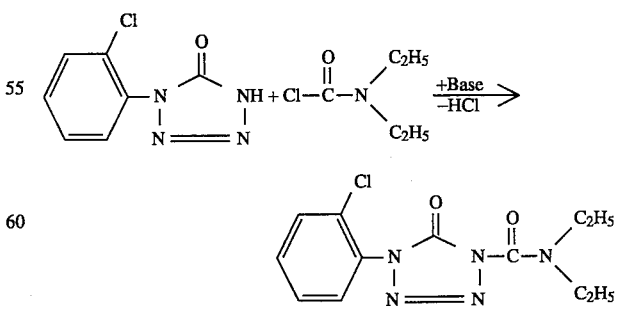

In the process a) according to the invention, the starting compounds of the formula (II) mean compounds based on the above definition of X and Y, preferably compounds based on the above preferred definitions of X and Y.

The compounds represented by the general Formula (II) can be prepared according to methods described in "The Journal of Organic Chemistry", Vol. 45, No. 21, 1980, pages 5130–5136 or "The Journal of American Chemical Society", Vol. 81, No. 7, 1980, pages 3076–3079.

As examples of the compounds represented by the general formula (II), there may be mentioned the following compounds:

1-(2-chlorophenyl)-5(4H)-tetrazolinone, 1-(2-chloro-6-methylphenyl)-5(4H)-tetrazolinone, and 1-(2,6-dichlorophenyl)-5(4H)-tetrazolinone.

In the process a) according to the invention, the starting compounds of the formula (III) mean compounds based on the above definition of $R^1$ and $R^2$, preferably compounds based on the above preferred definitions of $R^1$ and $R^2$.

The compounds of formula (III) are well known in the field of organic chemistry. As specific examples thereof, there may be mentioned:

Diethylcarbamoyl chloride,

Di-n-propylcarbamoyl chloride,

In carrying out the process a) mentioned above, use may be made, as suitable diluents, of any inert organic solvents.

Examples of such diluents are aliphatic, cycloaliphatic and aromatic, optionally chlorineted, hydrocarbons such as pentane, hexane, cyclohexane, petroleum ether, ligroin, benzene, toluene, xylene, dichloromethane, chloroform, carbon tetrachloride, 1,2-dichloroethane, chlorobenzene, dichlorobenzene and the like;

ethers such as diisopropyl ether, dibutyl ether, dioxane, dimethoxyethane (DME), tetrahydrofuran (THF), diethylene glycol dimethyl ether (DGM) and the like; nitriles such as acetonitrile, propionitrile and the like; acid amides such as dimethyl formamide (DMF), dimethyl acetamide (DMA), N-methylpyrrolidone, 1,3-dimethyl-2-imidazolidinone, hexamethylphosphoric triamide (HMPA) and the like; sulfones and sulfoxides such as dimethyl sulfoxide (DMSO), sulfolane and the like; and bases such as pyridine.

The above-mentioned process a) may be carried out in the presence of acid binder, and as the acid binder may be mentioned, for example, inorganic bases including hydroxides, carbonates, bicarbonates, alcolates, and hydrides of alkali metals, such as sodium hydrogen carbonate, potassium hydrogen carbonate, sodium carbonate, potassium carbonate, lithium hydroxide, sodium hydroxide, potassium hydroxide, calcium hydroxide, sodium methoxide, sodium ethoxide, potassim tert-buthoxide, lithium hydride, sodium hydride, potassium hydride, and the like; inorganic amides of alkali metals such as lithium amide, sodium amide, potassium amide and the like; and organic bases including tertiary amines, dialkylaminoanilines and pyridines, such as triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO), 1,8-diazabicyclo[ 5,4,0]-undec-7-ene (DBU) and the like. Furthermore, use may be made of organic lithium compounds such as, for example, methyl lithium, n-butyl lithium, sec-butyl lithium, tert-butyl lithium, phenyl lithium, dimethyl copper lithium, lithium diisopropyl amide, lithium cyclohexylisopropyl amide, lithium dicyclohexyl amide, n-butyl lithium.DABCO, n-butyl lithium.DBU, n-butyl lithium.TMEDA and the like.

In the above-mentioned process a), the reaction temperature can be varied within a substantially wide range. In general, the reaction is carried out at a temperature of from about −80° C. to about 200° C., preferably from about −30° C. to about 130° C.

Further, the reaction is preferably carried out under normal pressure, although it is also possible to employ a higher or reduced pressure.

When the above-mentioned process a) is carried out, use may be made, for example, of about 1.0 to 1.3 mols of the compounds of the general formula (III) in a diluent such as acetonitrile, for example, per mol of the compounds of the general formula (II) in the presence of 1 to 1.3 moler amounts of an acid binder to obtain be desired compounds.

The compounds represented by the general formula (I) according to the present invention can be used as herbicides for controlling paddy weeds.

Further, it has been discovered that a specially high herbicidal activity can be exhibited by herbicidal mixed compositions comprising, as active components, the compounds represented by the general formula (I) according to the present invention, together with at least one of the members selected from the group consisting of herbicidally active sulfonamides, herbicidally active pyrazoles, herbicidally active propioanilides, herbicidally active triazines, herbicidally active carbamates, herbicidally active diphenylethers, and herbicidally active acid amides.

Surprisingly, the herbicidal mixed compositions according to the present invention have been found to exhibit herbicidal effects substantially higher than the sum of the herbicidal effects that can be exhibited individually by the herbicidally active, respective components and, as a result, the concentration of each of the active compounds can be substantially reduced when practicing weed control operations, while, at the same time, a wide herbicidal spectrum can be obtained. Further, the herbicidal mixed compositions according to the present invention have been found to expand the period of application time and, for example, in paddy rice cultivation, exhibit excellent herbicidal effects for a period of from early stage of weed-emergence to weed-growing stage, with prolonged duration of activity and excellent residual effect, as well as phytotoxicity-free, excellent herbicidal effects on rice plants.

As specific examples of the herbicidal sulfonamides to be employed in the present herbicidal mixed compositions may be mentioned, for example, N-2-biphenylylsulfonyl N'-(4,6-dimethoxy-1,3,5-triazine-2-yl)-urea, ethyl 5-[3-(4,6-dimethoxypyrimidine-2-yl)ureidosulfonyl]- 1-methylpyrazole-4-carboxylate, methyl 2-[3-(4,6-dimethoxypyrimidine-2-yl)ureidosulfonylmethyl]benzoate, 3-(4,6-dimethoxy-1,3,5-triazine-2-yl)-1-[2-(2-methoxyethoxy)-phenylsulfonyl]urea, N-(2-chloroimidazole[1,2-a]pyridin -3-yl-sulfonyl)-N'-( 4,6-dimethoxy-2-pyrimidyl)urea, N'-(4,6-dimethoxypyrimidine-2-yl)-N"-(1-methylphenylsulfonylamino)-N" '-(4-ethoxycarbonyl-1-methylpyrazol 5-yl-sulfonyl)-guanidine, and N-(2-cyclopropylcarbonylphenylsulfamoyl)-N'-(4,6-dimethoxypyridin- 2-yl)urea.

The above-mentioned compounds are also well-known (see Japanese Patent Publication No. 481/1984, Japanese Patent Laid-open Nos. 112379/1982, 56452/1982, 22488/1984, 38091/1989 and 70475/1989).

As specific examples of herbicidally active pyrazoles to be employed in the present invention may be mentioned, for example, 4-(2,4-dichlorobenzoyl)-1,3-dimethylpyrazol-5-yl-p-toluenesulfonate, 2-[4- (2,4-dichlorobenzoyl)-1,3-dimethylpyrazol-5-yl]acetophenone, and P1 2-[4-(2,4-dichloro-m-toluoyl)-1,3-dimethylpyrazol-5-yloxy]- 4-methylacetophenone.

As specific examples of propionanilides to be employed in the present invention may be mentioned, for example, 2-(β-naphthyloxy)propioanilide, and (RS)-2-(2,4-dichloro-m-tolyloxy)propioanilide.

As specific examples of herbicidally active triazines to be employed in the present invention may be mentioned, for example, 2,4-bis(ethylamino)-6-(methylamino)-1,3,5-triazine, and 2-ethylamino-4-(1,2-dimethylpropylamino)-6-methylthio-1,3,5-triazine.

As specific examples of herbicidally active carbamates may be mentioned, for example, S-p-chlorobenzyl diethylthiocarbamate, S-1-methyl-1-phenylethyl piperidine-1-carbothioate, and S-benzyl 1,2-dimethylpropyl(ethyl)thiocarbamate.

As examples of herbicidally active diphenylethers to be employed in the present invention may be mentioned, for example, 2,4,6-trichlorophenyl-4'-nitrophenylether, and 2,4-dichlorophenyl-3'-methoxy-4'-nitrophenylether.

As examples of herbicidally active acid amides to be employed in the present invention may be mentioned, for example, (RS)-2-bromo-N-(α,α-dimethylbenzyl)-3,3-dimethylbutylamide.

The above-mentioned active compounds are known herbicidally active compounds that are disclosed in "Pesticide Manual", 1991, published by The British Crop Protect Council.

In the herbicidal mixed compositions according to the present invention, the mixing weight ratio of the active components may be varied in a relatively wide range.

In general, use may be made, per part by weight of the compounds represented by the general formula (I), of the herbicidal sulfonamides in the amount from 0.01 to 2 parts by weight, preferably from 0.05 to 1 part by weight; the herbicidally active pyrazoles in the amount of from 2.5 to 35 parts by weight, preferably from 3 to 15 parts by weight; the herbicidally active propioanilides in the amount of from 0.6 to 50 parts by weight, preferably from 2.0 to 28 parts by weight; the herbicidally active triazines in the amount of from 0.06 to 10 parts by weight, preferably from 0.15 to 6 parts by weight; the herbicidally active carbamates in the amount of from 3 to 15 parts by weight, preferably from 5 to 10 parts by weight; the herbicidally active diphenylethers in the amount of from 5 to 35 parts by weight, preferably from 7 to 15 parts by weight; and the herbicidally active acid amides in the amount of from 3.5 to 25 parts by weight, preferably from 4.0 to 10 parts by weight, respectively.

The mixed compositions according to the present invention exhibit a strong herbicidal activity; therefore the above-mentioned compositions may be used as herbicidal compositions and they may be advantageously used particularly as selective herbicidal compositions for paddy rice.

The herbicidal agents or mixed compositions according to the present invention can be applied, for example, to the following paddy field weeds (lowland weeds).

Dicotyledons of the following genera: Polygonum, Rorippa, Rotala, Lindernia, Bidens, Dopatrium, Eclipta, Elatine, Gratiola, Lindernia, Ludwigia, Oenanthe, Ranunculus, Deinostema.

Monocotyledons of the following genera: Echinochloa, Panicum, Poa, Cyperus, Monochoria, Fimbristylis, Sagittaria, Eleocharis, Scirpus, Alisma, Aneilema, Blyxa, Eriocaulon, Potamogeton.

The herbicidal agents or mixed compositions according to the present invention can be applied specifically, for example, to the following lowland weeds, in paddy fields.

| Botanical names | Latin names |
| --- | --- |
| Dicotyledons | |
| Rotala indica | Rotala indica Koehne |
| False pimpernel | Lindernia Procumbens Philcox |
| False loosestrife | Ludwigia prostrata Roxburgh |
| Largeleaf pondweed | Potamogeton distinctus A. Benn |
| American waterwort | Elatine triandia Schk |
| Dropwort | Oenanthe javanica |
| Monocotyledons | |
| Barnyard grass | Echinochloa oryzicola vasing |
| Monochoria | Monochoria vaginalis Presl |
| Matsubai | Eleocharis acicularis L. |
| Water chestnut | Eleocharis Kuroguwai Ohwi |
| Umbrella plant | Cyperus difformis L. |
| Mizugayatsuri | Cyperus serotinus Rottboel |
| Urikawa | Sagittaria pygmaea Miq |
| Narrowleaf waterplantain | Alisma canaliculatum A. Br. et Bouche |
| Bulrush | Scirpus junicoides Roxburgh |

However, the application of the herbicidal agents or mixed compositions according to the present invention is not limited to the above-mentioned weeds, but the application can be effected likewise also to other lowland weeds inhabiting paddy field weeds.

The present herbicidal agents or mixed compositions can be prepared into any conventional formulations. As such formulations there may be mentioned, for example, a liquid agent, an emulsion, a hydrated agent, a suspension, a powdery agent, a soluble powdery agent, a granular agent, a suspended emulsion concentrate, and microcapsules in a polymeric substance.

Those preparations can be prepared through well-known processes. The processes can be effected, for example, by mixing the active compounds with an extender, namely, with a liquid diluent and/or a solid diluent and,if required, with a surfactant, namely, with an emulsifier and/or a dispersant and/or a foaming agent.

In case of using water as an extender, for example, an organic solvent can also be used as an auxiliary solvent. As liquid diluents there may be mentioned, for example, aromatic hydrocarbons (such as xylene, toluene or alkylnaphthalene, etc.), chlorinated aromatic or chlorinated aliphatic hydrocarbons (such as chlorobenzenes, ethylene chlorides or methylene chloride, etc.), aliphatic hydrocarbons [such as cyclohexane, etc., or paraffins (for example, mineral-oil fractions, mineral or vegetable oils)], alcohols (such as butanol, glycol and ethers and esters thereof, etc.), ketones (such as acetone, methyl ethyl ketone, methyl isobutyl ketone or cyclohexanone, etc.), strong polar solvents (such as dimethylformamide and dimethyl sulfoxide, etc.), and water can also be mentioned as a liquid diluent.

As solid diluents may be mentioned ammonium salts, and natural soily minerals (such as kaolin, clay, talc, chalk, quartz, attapulgite, montmorillonite, or diatomite,etc.) and soil synthetic minerals (such as highly dispersive silicic acid, alumina, silicate, etc.). And as solid carriers for granular agents there can be mentioned powdered and fractionated rocks (such as calcite, marble, ptunice stone, meerschaum, dolomite, etc.), synthetic grains of organic or inorganic powders, and fine particles of organic substances (such as saw dust, coconut-shells, corn ear-stems, and tobacco stalks, etc.).

As emulsifiers and/or foaming agents may be mentioned nonionic and anionic emulsifiers such as, for example, polyoxyethylene fatty acid esters, polyoxyethylene fatty alcohol ethers such as, for example, alkylaryl polyglycol ethers, alkyl sulfonates, alkyl sulfates, aryl sulfonates, etc., and albumin hydrolysates.

As dispersants, for example, lignin-sulfite waste liquor and methyl cellulose are suitable.

Adhesives or stickers may also be used in the formulations in the form of powdery agent, granular agent, jambo agent, or emulsion, and as adhesives or stickers may be mentioned carboxy methyl cellulose, natural and synthetic polymers (such as gum arabic, polyvinyl alcohol, and polyvinyl acetate, etc., for example), natural phosphatides (such as cephalins and lecithins) and synthetic phosphatides. Further as additives there may also be used mineral and vegetable oils.

Colorants may also be used, such as inorganic pigments (such as, for example, iron oxide, titanium oxide and Prussian blue), and organic dyes such as, for example, alizarin dye, azo dye, and metallic phthalocyanine pigments, and further a trace amount of such elements as salts of iron, manganese, boron, copper, cobalt, molybdenum and zinc.

The formulation contains generally 0.1–95% by weight, preferably 0.5–90% by weight of the active compound.

In order to control weeds, the active compounds of the herbicidal agents and herbicidals mixed compositions according to the present invention can be used as such, or in the form of formulations thereof, and the mixture can be handled-in the form of formulations or in the form of a tank-mixture.

The active compound according to the present invention can be used as a mixture with other well-known active compounds, that is, with active compounds normally used for paddy fields such as, for example, bactericides, insecticides, plant-growth regulators, plant nutritive agents, soil conditioners, stabilizers and any other herbicides.

Advantageously, as a specific example, herbicidal mixed compositions according to the present invention there may be included, per part by weight of the herbicidal sulfonamides from 1 to 200 parts by weight, preferably from 2 to 100 parts by weight of a stabilizer such as 1-(α,α-dimethylbenzyl)-3-p-tolylurea.

The present active compounds can be used as such, as their formulations or as the use forms prepared therefrom by further dilution thereof, such as in the forms of ready-to-use solutions, emulsions, suspensions, powders, wettable powders, pastes and granules.

They may be used in the customary manner, for example, by watering, spraying, atomizing, dusting, scattering, etc.

The present active compounds can be used either in the pre-, or post-emergence period of plants. It is also possible to apply the active compounds into soil before the seeds of plants are sown.

The concentration of active compound used in the present herbicidal agents can vary within a substantially wide range. It depends essentially on the nature of the desired effect. In general, the amounts used as a herbicide are from about 0.01 to about 10 kg of active compound per hectare, preferably from about 0.1 to about 2 kg/ha.

The dosages of the present herbicidal mixed compositions may be varied within a substantially wide range, viz., from 0.1 to 5 kg/ha and preferably from 0.2 to 3 kg/ha in terms of the amount of active compounds.

The preparation and the use of the active compounds according to the present invention are shown in the following examples, which are merely illustrative and not limiting,

EXAMPLES

SYNTHESIS EXAMPLES

EXAMPLE 1

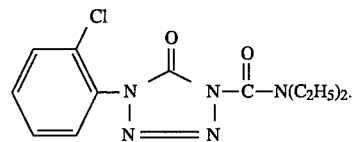

1(2-chlorophenyl)-5(4H)-tetrazolinone (2 g) and potassium carbonate (1.87 g) were suspended in acetonitrile (30 ml), followed by a fifteen minute refluxing. After cooling, diethylcarbamoyl chloride (1.84 g) was added to the reaction mixture, followed by a further five hours refluxing. The resulting salt was removed by filtration and the solvent was evaporated. The resulting residue was purified by flush column chromatography (hexane:ethyl acetate=5:2), to obtain the desired 1-(2-chlorophenyl)-4-(N,N-diethylcarbamoyl)-5(4H)-tetrazolinone (2.33 g). $n_D^{20}$ 1.5415.

Particulars of Example 1 and other compounds obtained by the same method are shown in Table 1.

TABLE 1

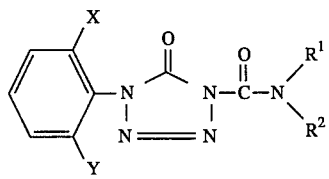

| Compound No. | X | Y | $R^1$ | $R^2$ | physico-chemical data |
|---|---|---|---|---|---|
| 1 | Cl | H | $C_2H_5$ | $C_2H_5$ | $n_D^{20}$ 1.5415 |
| 2 | Cl | H | $C_3H_7$-n | $C_3H_7$-n | $n_D^{20}$ 1.5323 |
| 3 | Cl | Cl | $C_2H_5$ | $C_2H_5$ | mp. 69.5–71.5° C. |
| 4 | Cl | Cl | $C_3H_7$-n | $C_3H_7$-n | $n_D^{20}$ 1.5403 |
| 5 | Cl | $CH_3$ | $C_2H_5$ | $C_2H_5$ | $n_D^{20}$ 1.5282 |
| 6 | Cl | $CH_3$ | $C_3H_7$-n | $C_3H_7$-n | $n_D^{20}$ 1.5248 |
| 7 | Br | H | $C_2H_5$ | $C_2H_5$ | $n_D^{20}$ 1.5510 |
| 8 | Br | Br | $C_2H_5$ | $C_2H_5$ | mp. 122.5–128.5° C. |
| 9 | Br | Br | $C_3H_7$-n | $C_3H_7$-n | $n_D^{20}$ 1.5605 |
| 10 | Br | H | $C_3H_7$-n | $C_3H_7$-n | $n_D^{20}$ 1.5410 |
| 11 | Cl | $CH_3$ | $C_3H_7$-n | $C_2H_5$ | $n_D^{20}$ 1.5312 |
| 12 | Cl | $CH_3$ | $C_2H_5$ | $C_4H_9$-sec | |
| 13 | Cl | $CH_3$ | $C_3H_7$-n | $C_4H_9$-sec | $n_D^{20}$ 1.5248 |
| 14 | Cl | $CH_3$ | $C_2H_5$ | $C_4H_9$-n | $n_D^{20}$ 1.5291 |
| 15 | Cl | $CH_3$ | $C_2H_5$ | $C_3H_7$-iso | $n_D^{20}$ 1.5288 |
| 16 | Cl | $CH_3$ | $C_3H_7$-iso | $C_3H_7$-iso | $n_D^{20}$ 1.5220 |
| 17 | Cl | $CH_3$ | $C_4H_9$-n | $C_4H_9$-n | $n_D^{20}$ 1.5202 |
| 18 | Cl | $CH_3$ | $C_4H_9$-iso | $C_4H_9$-iso | $n_D^{20}$ 1.5145 |

EXAMPLE 2 (Synthesis of Intermediate Compound)

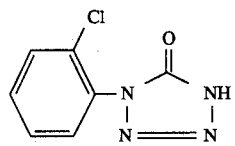

2-chlorophenylisocyanate (7 g) and trimethylsilyl azide (7.9 g) were mixed and heated under refluxing for eight hours. The excessive trimethylsilyl azide was distilled off under reduced pressure and to the residue there were added 40 ml of methanol. Thereafter, the methanol was evaporated and the residue was purified by flush column chlomatography (hexane:ethyl acetate=2:1) to obtain the desired 1-( 2-chlorophenyl)-5(4H)-tetrazolinone (7 g) having a melting point in the range of from 124.5° to 125.5° C.

BIOTEST EXAMPLE

Comparative compound

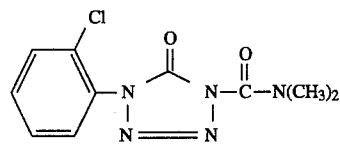

C-1

(disclosed in U.S. Pat. No. 956,469 and EP-A-146,279, Example 7 in both references).

TEST EXAMPLE 3

Test on herbicidal activity against lowland weeds

Formulation of Active Compounds

Carrier: 5 parts by weight of acetone

Emulsifier: 1 part by weight of benzyloxy polyglycol ether

To produce a suitable preparation of each of the active compounds, 1 part by weight of an active compound was mixed with the stated amount of carrier and with the stated amount of emulsifier, and the resulting emulsifiable concentrate was then diluted with water to the desired concentrations.

Test Procedures

Each of several pots, having a size of 25×20×9 cm and an area of 1/2,000 are, was filled with soil taken from a paddy field. Paddy-rice plant seedlings (Nihonbare Variety) each of the 2.5-leaf stage, with a height of 15 cm, were transplanted with three seedlings per hill at two zones in each of the pots.

Then, seeds of the following weeds were sown in the soil, which was kept under wet conditions:

barnyard grass (Echinochloa);

flatsedge (Cyperus);

monochoria (Monochoria);

broad-leaved weeds such as false pimpernel (Lindernia), toothcup (Rotala), elatine (Elatine), ammannia (Ammannia), and dopatrium (Dopatrium); and

*Scirpus juncoides* Roxb var. *Hotarui Ohwi* (Scirpus).

Then, water was supplied the pots to a depth of 2–3 cm, above the soil surface.

Seven days after transplanting of the rice plants, the formulation of each of the active compounds, which had been prepared in the manner mentioned above, was applied to each of the pots in a submerged application manner. After that, the water depth was kept to a height of about 3 cm.

Three weeks after the application of the active compound, the degree of damage to the weeds and the degree of phytotoxicity on the rice plants were determined, and recorded 100% indicating complete death and 0% indicating herbicidal effect.

The test results are shown in Table 2.

TABLE 2

| Test Compound | Dosage of Active Compound kg/ha | Herbicidal effect | | | | | | Phytotoxicity Rice |
|---|---|---|---|---|---|---|---|---|
| | | Echi-nochloa | Cyperus | Scirpus | Monochoria | Broad leaf weeds | Sagittaria | |
| 1 | 0.3 | 100 | 100 | 100 | 100 | 100 | 0 | 30 |
|   | 0.15 | 70 | 100 | 80 | 80 | 60 | 0 | 0 |
| 2 | 0.3 | 100 | 100 | 100 | 100 | 100 | 0 | 20 |
|   | 0.15 | 80 | 100 | 70 | 90 | 70 | 0 | 0 |
| 3 | 0.3 | 100 | 100 | 100 | 100 | 100 | 20 | 25 |
|   | 0.15 | 80 | 100 | 80 | 90 | 70 | 0 | 0 |
| 4 | 0.3 | 100 | 100 | 90 | 100 | 80 | 20 | 20 |
|   | 0.15 | 80 | 100 | 80 | 90 | 70 | 0 | 0 |
| 5 | 0.3 | 100 | 100 | 100 | 100 | 90 | 0 | 25 |
|   | 0.15 | 80 | 100 | 80 | 90 | 70 | 0 | 0 |
| 6 | 0.3 | 100 | 100 | 100 | 100 | 100 | 50 | 20 |
|   | 0.15 | 80 | 100 | 80 | 90 | 70 | 0 | 0 |
| 7 | 0.3 | 100 | 100 | 90 | 100 | 80 | 0 | 20 |
|   | 0.15 | 70 | 100 | 80 | 90 | 50 | 0 | 0 |
| 8 | 0.3 | 100 | 100 | 100 | 100 | 100 | 10 | 15 |
|   | 0.15 | 70 | 100 | 80 | 90 | 70 | 0 | 0 |
| 13 | 0.3 | 100 | 100 | 100 | 100 | 100 | 20 | 10 |
|   | 0.15 | 80 | 100 | 100 | 100 | 100 | 0 | 0 |
| Comparative | | | | | | | | |
| C-1 | 0.3 | 40 | 90 | 70 | 40 | 60 | 0 | 0 |

TABLE 2-continued

| Test Compound | Dosage of Active Compound kg/ha | Herbicidal effect | | | | | | Phytotoxicity Rice |
|---|---|---|---|---|---|---|---|---|
| | | Echinochloa | Cyperus | Scirpus | Monochoria | Broad leaf weeds | Sagittaria | |
| | 0.15 | 20 | 70 | 50 | 30 | 20 | 0 | 0 |

EXAMPLE 4 (Biotest)

Test for determining herbicidal effect of the present herbicidal compositions on lowland weeds Into a plurality of pots (25×20×9 cm) each having 1/2000 are filled with paddy field soil, while paddy rice seedlings (species: NIHONBARE) at 2.5 leaf stage (stalk height of 15 cm) were transplanted with three seedlings per unit at two separate sections in each of the pots.

Then, the tubers of *Sagittaria pygmaea Miq* and small pieces of Spikerrush (*Eleocharis acicularis*) as well as the seeds of the following respective weeds were inoculated into the respective pots and filled with water to a height of about 2 to 3 cm above the soil surface:

*Echinochloa oryzicola rasing,*

*Cyperus difformis L.,*

*Monochoria vaginalis Presl,*

Broad leaved weeds such as *Lindernia pyxidaria, Rotala indica Koehne,* American waterwort (*Elatine orientalis Makino*), Ammannia multiflora Roxburgh, *Dopatrium junceum* Hamilton, Bulrush, *Scirpus juncoides* and Roxburgh.

Seven days after the paddy rice transplanting, the following active compound and mixtures according to the present invention were applied to the respective pots by water-surface treatment.

After the treatment, the water layer in each of the pots was kept at a height of about 3 cm and three weeks after the treatment, the herbicidal effects and degrees of phytotoxicity were evaluated by the following percentage scale:

100%: Completely killed

0%: No effect or no phytotoxicity

The results are shown in the following Table 3:

In Table 3, A, B, C, D, E, F and G in the herbicidal compositions represent the following active compounds, respectively:

A: Methyl 2-[3-(4,6-dimethoxypyrimidin-2-yl) ureidosulfonylmethyl]benzoate,

B: Ethyl 5-[3-(4,6-dimethoxypyrimidin-2-yl) ureidosulfonyl]-1-methylpyrazole-4-carboxylate, C: N-(2-chloroimidazole[1,2-a]pyridin-3-yl-sulfonyl)-N'-( 4,6-dimethoxy-2-pyrimidyl)urea, D: 4-(2,4-dichlorobenzoyl)-1,3-dimethyl-5-pyrazolyl-p-toluenesulfonate, E: 2-(β-naphthyloxy)propionanilide, F: 2-ethylamino-4-(1,2-dimethyl propylamino)-6-methylthio- 1,3,5-triazine, G: S-p-chlorobenzyl diethylthiocarbamate.

TABLE 3

| Test Comp. | Dosage of active compound kg/ha | Herbicidal Effect | | | | | | | Phytotoxicity Rice |
|---|---|---|---|---|---|---|---|---|---|
| | | Echinochloa | Cyperus | Monochoria | Broad leaf Weeds | Scirpus | Sagittaria | Spikerrush (Eleocharis acicularis) | |
| 1 + B | 0.15 + 0.021 | 100 | 100 | 100 | 100 | 100 | 100 | — | 0 |
| 4 + A | 0.15 + 0.075 | 100 | 100 | 100 | 100 | 100 | 100 | — | 0 |
| 4 + B | 0.15 + 0.021 | 100 | 100 | 100 | 100 | 100 | 100 | — | 0 |
| 6 + A | 0.15 + 0.075 | 100 | 100 | 100 | 100 | 100 | 100 | — | 0 |
| 6 + B | 0.15 + 0.021 | 100 | 100 | 100 | 100 | 100 | 100 | — | 0 |
| 6 + C | 0.15 + 0.09 | 100 | 100 | 100 | 100 | 100 | 100 | — | 0 |
| 3 + D | 0.15 + 1.8 | 100 | 100 | 100 | 100 | 100 | 100 | — | 0 |
| 5 + E | 0.15 + 2.1 | 100 | 100 | 100 | 100 | 100 | 100 | — | 0 |
| 6 + F | 0.15 + 0.33 | 100 | 100 | 100 | 100 | — | — | 100 | 0 |
| 6 + G (*1) | 0.1 + 1.5 | 100 | — | — | — | — | — | — | 0 |
| 1 | 0.15 | 70 | 100 | 80 | 80 | 60 | 0 | — | 0 |
| 3 | 0.15 | 80 | 100 | 80 | 90 | 70 | 0 | — | 0 |
| 4 | 0.15 | 80 | 100 | 80 | 90 | 70 | 0 | — | 0 |
| 5 | 0.15 | 80 | 100 | 80 | 90 | 70 | 0 | — | 0 |
| 6 | 0.15 | 80 | 100 | 80 | 90 | 70 | 0 | — | 0 |
| 6 (*2) | 0.1 | 70 | — | — | — | — | — | — | 0 |
| A | 0.075 | 40 | 100 | 100 | 100 | 100 | — | — | 0 |
| B | 0.021 | 50 | 100 | 100 | 100 | 100 | — | — | 0 |
| C | 0.09 | 50 | 100 | 100 | 100 | 100 | — | — | 0 |
| D | 1.8 | 60 | 100 | 100 | 80 | 60 | 100 | — | 0 |

TABLE 3-continued

| Test Comp. | Dosage of active compound kg/ha | Echi-nochloa | Cyperus | Mono-choria | Broad leaf Weeds | Scirpus | Sagit-taria | Spiker-rush (Eleo-charis acicu-laris) | Phytoto-xicity Rice |
|---|---|---|---|---|---|---|---|---|---|
| E | 2.1 | 60 | 100 | 100 | 100 | 100 | 100 | — | 0 |
| F | 0.33 | 40 | 100 | 100 | 100 | — | — | 80 | 0 |
| G (*3) | 1.5 | 80 | — | — | — | — | — | — | 0 |

In Table 3, the composition G&G indicated by (*1) controlled the emergence of Barnyard grass for a period of forty-eight days, while the compound No. 6 indicated by (*2) controlled said emergence for a period of forty days, and the compound G (*3) controlled said emergence for a period of twenty-five days.

It will be understood that the specification and examples are illustrative but not limitative of the present invention and that other embodiments within the spirit and scope of the invention will suggest themselves to those skilled in the art.

We claim:

1. A herbicidal composition comprising (A) a tetrazolinone of the formula

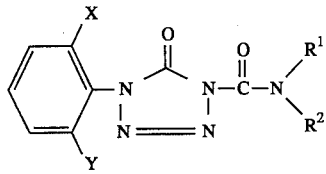

wherein

X is chlorine or bromine,

Y is hydrogen, chlorine, bromine, methyl or ethyl, and $R^1$ and $R^2$ each independently is $C_{2-4}$ alkyl and (B) at least one herbicide selected from the group consisting of a sulfonamide pyrazole propionanilide, triazine, carbamate, diphenyl ether and acid amide.

2. A composition according to claim 1, wherein

X is chlorine,

Y is hydrogen, chlorine or methyl, and $R^1$ and $R^2$ each independently is ethyl, n-propyl, isopropyl, n-butyl, isobutyl or sec-butyl.

3. A composition according to claim 1, wherein (A) is 1-(2-chlorophenyl)-4-(N,N-diethylcarbamoyl)-5(4H)-tetrazolinone of the formula

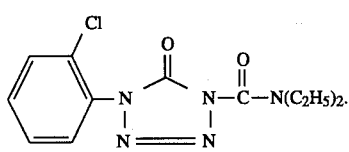

4. A composition according to claim 1, wherein (A) is 1-(2,6-dichlorophenyl)-4-(N N-di-n-propylcarbamoyl)-5 (4H) -tetrazolinone of the formula

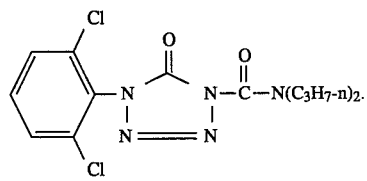

5. A composition according to claim 1, wherein (A) is 1-(2-chloro-6-methylphenyl) -4-(N,N-di-n-propylcarbamoyl)-5(4H)-tetrazolinone of the formula

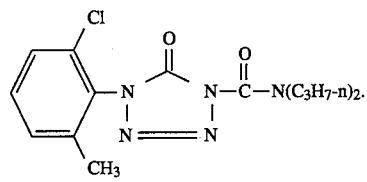

6. A herbicidal composition according to claim 5, wherein (B) is methyl 2-[3-(4,6-dimethoxypyrimidin-2-yl) ureidosulfonylmethyl]benzoate.

7. A method of combating unwanted vegetation which comprises applying to such vegetation or to a locus from which it is desired to exclude such vegetation a herbicidally effective amount of a composition according to claim 6.

8. A composition according to claim 1, wherein (A) is 1-(2-chloro-6-methylphenyl)-4-(N-sec-butyl-N-n-propyl-carbamoyl)-( 5(4H)-tetrazolinone of the formula

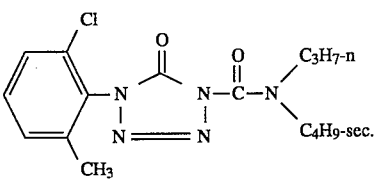

9. A composition according to claim 1, wherein (B) comprises at least one member selected from the group consisting of N-2-biphenylylsulfonyl N'-(4,6-dimethoxy-1,3,5-triazine-2-yl)urea, ethyl 5-[3-(4,6-dimethoxypyrimidine-2-yl) ureidosulfonyl]- 1-methylpyrazole-4-carboxylate, methyl 2-[3-(4,6-dimethoxypyrimidine-2-yl) ureidosulfonylmethyl] benzoate, 3-(4,6-dimethoxy-1,3,5-triazine-2-yl)-1-[2-( 2-methoxyethoxy)phenylsulfonyl]urea, N-(2-chloroimidazole[1,2-a]pyridine-3-yl-sulfonyl)-N'-(4,6-dimethoxy-2-pyrimidyl)urea, N'-(4,6-dimethoxypyrimidine-2-yl)-N''-(4-methylphenylsulfonylamino)-N'''-(4-ethoxycarbonyl-1-methylpyrazole-5-yl-sulfonyl)guanidine, and N-(2-cyclopropylcarbonylphenylsulfamoyl)-N'-(4,6-dimethoxypyridine-2-yl)urea.

10. A composition according to claim 1 wherein (B) comprises at least one member selected from the group consisting of S-p-chlorobenzyl diethylthiocarbamate, S-1-methyl-1-phenylethyl piperidine-1-carbothioate, and S-benzyl 1,2-dimethyl-propyl(ethyl)thiocarbamate.

11. A composition according to claim 1, wherein (B) comprises at least one member selected from the group consisting of 2,4,6-trichlorophenyl-4'-nitrophenylether, and 2,4-dichlorophenyl-3'-methoxy-4-nitrophenylether.

12. A composition according to claim 1, wherein (B) comprises (RS)-2-bromo-N-(α,α-dimethylbenzyl)-3,3-dimethylbutylamide.

13. A composition according to claim 1, wherein (B) comprises at least one member selected from the group consisting of 4-(2,4-dichlorobenzoyl)-1,3-dimethylpyrazole-5-yl-p-toluene sulfonate, 2-[4-(2,4-dichlorobenzoyl)-1,3-dimethylpyrazole-5-yl]-acetophenone, and 2-[4-(2,4-dichloro-m-toluoyl)-1,3-dimethylpyrazole-5-yloxy]-4-methylacetophenone.

14. A composition according to claim 1, wherein (B) comprises at least one member selected from the group consisting of 2-(β-naphthyloxy)propionanilide and (RS)-2-(2,4-dichloro-m-tolyloxy)propionanilide.

15. A composition according to claim 1, wherein (B) comprises at least one member selected from the group consisting of 2,4-bis(ethylamino)-6-(methylamino)-1,3,5-triazine and 2-ethylamino-4-(1,2-dimethylpropylamino)-6-methylthio-1,3,5-triazine.

16. A herbicidal composition according to claim 1, wherein per part by weight of herbicide (A) as the herbicide (B) there is present about 0.01 to 2 parts by weight of the sulfonamide 2.5 to 35 parts by weight of the pyrazole, 0.6 to 50 parts by weight of the propionanilide, 0.06 to 10 parts by weight of the triazine, 3 to 15 parts by weight of the carbamate, 5 to 35 parts by weight of the diphenylether, or 3.5 to 25 parts by weight of the acid amide.

17. A method of combating unwanted vegetation which comprises applying to such vegetation or to a locus from which it is desired to exclude such vegetation a herbicidally effective amount of a composition according to claim 1.

* * * * *